United States Patent
Heilmann et al.

(10) Patent No.: US 12,403,078 B2
(45) Date of Patent: Sep. 2, 2025

(54) DYEING COMPOSITION IN AQUEOUS-ALCOHOLIC MEDIUM

(71) Applicant: KAO CORPORATION, Tokyo (JP)

(72) Inventors: Jens Heilmann, Darmstadt (DE); Sandra Schmelz, Darmstadt (DE); Jonathan Wood, Darmstadt (DE)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 18/841,456

(22) PCT Filed: Feb. 24, 2023

(86) PCT No.: PCT/EP2023/054691
§ 371 (c)(1),
(2) Date: Aug. 26, 2024

(87) PCT Pub. No.: WO2023/161423
PCT Pub. Date: Aug. 31, 2023

(65) Prior Publication Data
US 2025/0161179 A1  May 22, 2025

(30) Foreign Application Priority Data
Feb. 28, 2022  (EP) .................... 22159138

(51) Int. Cl.
| | |
|---|---|
| *A61Q 5/10* | (2006.01) |
| *A61K 8/34* | (2006.01) |
| *A61K 8/39* | (2006.01) |
| *A61K 8/41* | (2006.01) |

(52) U.S. Cl.
CPC .............. *A61K 8/416* (2013.01); *A61K 8/345* (2013.01); *A61K 8/39* (2013.01); *A61Q 5/10* (2013.01); *A61K 2800/596* (2013.01); *A61K 2800/882* (2013.01)

(58) Field of Classification Search
CPC .......... A61K 8/416; A61K 8/345; A61K 8/39; A61K 2800/596; A61K 2800/882; A61Q 5/10
USPC .......................................................... 8/405
See application file for complete search history.

(56) References Cited

U.S. PATENT DOCUMENTS

| | | | |
|---|---|---|---|
| 2011/0236328 A1 | 9/2011 | Sasao et al. | |
| 2018/0369103 A1 * | 12/2018 | Owens | .............. A61K 8/817 |

FOREIGN PATENT DOCUMENTS

| | | | | |
|---|---|---|---|---|
| CN | 111372562 A * | 7/2020 | .............. | A61Q 5/10 |
| EP | 3659578 A1 * | 6/2020 | .............. | A61Q 5/10 |
| EP | 3 741 352 A1 | 11/2020 | | |
| WO | WO 99/36047 A1 | 7/1999 | | |
| WO | WO 02/39970 A1 | 5/2002 | | |
| WO | WO 2005/063179 A1 | 7/2005 | | |
| WO | WO 2010/023560 A2 | 3/2010 | | |
| WO | WO 2015180739 A1 * | 12/2015 | .............. | A61Q 5/10 |

OTHER PUBLICATIONS

International Search Report & Written Opinion mailed on May 3, 2023 in PCT/EP2023/054691 filed on Feb. 24, 2023 (11 pages).
Extended European Search Report mailed Sep. 12, 2022 in EP Application No. 22159138.1 (12 pages).
Database GNPD [Online] MINTEL; Oct. 28, 2021 (Oct. 28, 2021), anonymous: "Permanent Colour", XP055956181, Database accession No. 9083838, 5 pages.
Database GNPD [Online] MINTEL; Jul. 2, 2012 (Jul. 2, 2012), anonymous: "Permanent Cream Gel Colourant", XP055956719, Database accession No. 1822540, 7 pages.
Olivier J. X. Morel et al: "Current Trends in the Chemistry of Permanent Hair Dyeing", Chemical Reviews, vol. 111, No. 4, Apr. 13, 2011, pp. 2537-256.
Anonymous: "NEODOL™ 25-3 Technical Datasheet", Nov. 2020 (Nov. 1, 2020), XP055956341, 2 pages.
Fisher Kevin: "Final Report on the Safety Assessment of Nonoxynols-2, -4, -8, -9, -10, -12, -14, -15, -30, -40, and -50", Journal of the American College of Toxicology, vol. 2, No. 7, Jan. 1, 1983, pp. 35-60.

* cited by examiner

Primary Examiner — Eisa B Elhilo
(74) Attorney, Agent, or Firm — Oblon, McClelland, Maier &Neustadt, L.L.P.

(57) ABSTRACT

A dyeing composition for keratin fibers having a pH of 6 to 12 comprising a hair dye, 5 wt. % or more of a $C_2$-$C_4$ alcohol, a non-ionic surfactant having an HLB value of 11 or less, a quaternary ammonium surfactant according to Formula (I):

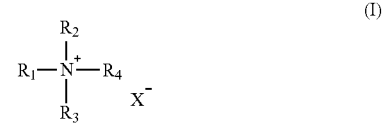

wherein $R_1$ is a $C_{17}$ to $C_{22}$ alkyl or alkylene group, $R_2$ is a $C_1$ to $C_{22}$ alkyl or alkylene group, $R_3$ and $R_4$ are each independently a $C_1$ to $C_4$ alkyl or alkylene group, and $X^-$ is a halide, sulfate, or methosulfate anion, and 0.5 to 10 wt. % of a quaternary ammonium surfactant according to Formula (II):

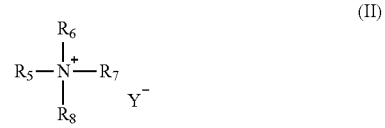

wherein $R_5$ is a $C_8$ to $C_{16}$ alkyl or alkylene group, $R_6$ is a $C_1$ to $C_{16}$ alkyl or alkylene group, $R_7$ and $R_8$ are each independently a $C_1$ to $C_4$ alkyl or alkylene group, and $Y^-$ is a halide, sulfate or methosulfate anion.

20 Claims, No Drawings

DYEING COMPOSITION IN AQUEOUS-ALCOHOLIC MEDIUM

CROSS-REFERENCE TO RELATED APPLICATIONS

This application is a National Phase entry under 35 U.S.C. § 371 of PCT Application PCT/EP2023/054691, filed on Feb. 24, 2023, which claims the benefit of priority to European Patent Application No. EP 22159138.1.5, filed on Feb. 28, 2022, the entire contents of each of which are incorporated herein by reference.

FIELD OF THE INVENTION

The present invention is directed to a dyeing composition for keratin fibers in aqueous-alcoholic medium comprising dyes as well as certain surfactants.

BACKGROUND OF THE INVENTION

Conventional liquid hair dyeing compositions with low viscosity employ ethoxylated surfactants, which are dissolved in an aqueous-alcoholic medium with the help of anionic surfactants. After mixing with a second agent, spontaneous gel formation occurs leading to a viscosity increase that allows for safe application to the consumer's hair without dripping. However, the resulting ready-to-use composition leaves a poor hair feel, thereby leading to dissatisfaction of the consumers.

Hair feel usually is increased by cationic surfactants. However, combining non-ionic surfactants in aqueous-alcoholic compositions with cationic surfactants commonly leads to stability problems in the ready-to-use composition, leading to dripping of the composition onto the consumer's head er even into the face during color application.

The prior art has not yet solved the dripping problem of the ready-to-use mixture resulting from previously liquid compositions with water-like viscosity while increasing the cosmetic appearance of the colored hair.

SUMMARY OF THE INVENTION

Therefore, the first object of the present invention is an aqueous-alcoholic dyeing composition A for keratin fibers, preferably for human keratin fibers, more preferably for human hair, having a pH in the range of 6 to 12 comprising:
  a) one or more hair dye(s),
  b) one or more $C_2$-$C_4$ monohydric, dihydric, or trihydric alcohol(s), and/or their mixtures,
  c) one or more non-ionic surfactant(s) having an HLB value of 11 or less,
  d) one or more quaternary ammonium surfactant(s) according to the following structure:

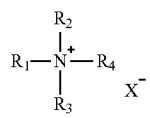

wherein $R_1$ and $R_2$ are independently selected from $C_1$ to $C_{22}$ alkyl or alkylene with the provision that at least $R_1$ is selected from $C_{17}$ to $C_{22}$ alkyl or alkylene, $R_3$ and $R_4$ are independently selected from $C_1$ to $C_4$ alkyl or alkylene, and $X^-$ is a halogen, sulfate or methosulfate anion, wherein the total concentration of compound(s) according to group b) is 5% by weight or more, calculated to the total weight of composition A, wherein composition A comprises one or more quaternary ammonium surfactant(s) according to the following structure as compound(s) according to group e):

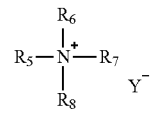

wherein $R_5$ and $R_6$ are independently selected from $C_1$ to $C_{16}$ alkyl or alkylene with the provision that at least $R_5$ is selected from $C_8$ to $C_{16}$ alkyl or alkylene, $R_7$ and $R_8$ are independently selected from $C_1$ to $C_4$ alkyl or alkylene, and $Y^-$ is a halogen, sulfate or methosulfate anion, and wherein the total concentration of one or more compound(s) according to group e) is in the range of 0.5% to 10% by weight, calculated to the total weight of composition A.

The second object of the present invention is a kit-of-parts for dyeing keratin fibers, preferably for dyeing human keratin fibers, more preferably for dyeing human hair, comprising:
  composition A as defined above,
  an aqueous acidic composition B having a pH in the range of 1 to 6 and optionally comprising one or more oxidizing agent(s), preferably hydrogen peroxide,
  an optional bleaching composition C.

The third object of the present invention is a ready-to-use composition having a pH in the range of 6 to 12 comprising composition A as defined above and composition B as defined above.

The fourth object of the present invention is a method for dyeing keratin fibers, preferably human keratin fibers, more preferably human hair, comprising the steps of:
  i) mixing composition A as defined above with an acidic aqueous composition B as defined above to yield a ready-to-use composition having a pH in the range of 6 to 12,
  ii) applying the ready-to-use composition onto keratin fibers and leaving it for a time period in the range of 1 to 60 min,
  iii) rinsing off the ready-to-use composition,
  iv) optionally shampooing and drying the keratin fibers.

DETAILED DESCRIPTION OF THE INVENTION

Inventors of the present invention have surprisingly found out that a composition according to claim 1 delivers superior dry and wet hair feel, superior storage stability and low to no tendency of dripping from the consumer's hair during color applications.

Dyeing Composition

The present invention is directed to an aqueous-alcoholic dyeing composition A for keratin fibers, preferably for human keratin fibers, more preferably for human hair, having a pH in the range of 6 to 12 comprising:
  a) one or more hair dye(s),
  b) one or more $C_2$-$C_4$ monohydric, dihydric, or trihydric alcohol(s), and/or their mixtures,
  c) one or more non-ionic surfactant(s) having an HLB value of 11 or less, d) one or more quaternary ammonium surfactant(s) according to the following structure:

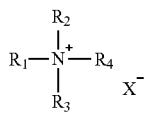

wherein $R_1$ and $R_2$ are independently selected from $C_1$ to $C_{22}$ alkyl or alkylene with the provision that at least $R_1$ is selected from $C_{17}$ to $C_{22}$ alkyl or alkylene, $R_3$ and $R_4$ are independently selected from $C_1$ to $C_4$ alkyl or alkylene, and $X^-$ is a halogen, sulfate or methosulfate anion, wherein the total concentration of compound(s) according to group b) is 5% by weight or more, calculated to the total weight of composition A, wherein composition A comprises one or more quaternary ammonium surfactant(s) according to the following structure as compound(s) according to group e):

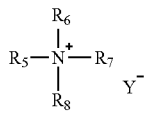

wherein $R_5$ and $R_6$ are independently selected from $C_1$ to $C_{16}$ alkyl or alkylene with the provision that at least $R_5$ is selected from $C_8$ to $C_{16}$ alkyl or alkylene, $R_7$ and $R_8$ are independently selected from $C_1$ to $C_4$ alkyl or alkylene, and $Y^-$ is a halogen, sulfate or methosulfate anion, and wherein the total concentration of one or more compound(s) according to group e) is in the range of 0.5% to 10% by weight, calculated to the total weight of composition A.

It is preferred from the viewpoint of dyeing intensity and cosmetic safety that the pH of composition A is 7 or more, more preferably it is 7.5 or more, still more preferably it is 8 or more.

It is preferred from the viewpoint of cosmetic safety that the pH of composition A is 11 or less and more preferably 10.5 or less.

For attaining the above-mentioned effects, it is preferred that the pH of composition A is in the range of 7 to 11, more preferably in the range of 7.5 to 10.5, further more preferably in the range of 8 to 10.5.

For the purpose of the present invention, the pH is measured with a glass electrode at 25° C. under atmospheric pressure.

It is preferred from the viewpoint of stability that composition A is transparent judged by the naked human eye at an optical path length of 1 cm.

Alternatively, transparency of the composition may be measured by UV-Vis spectrometry at 600 nm at an optical path length of 1 cm. The composition is transparent if the light transmission is 80% or more.

It is further preferred from the viewpoint of cosmetic applicability that the viscosity of composition A prior to mixing with composition B is 1,000 mPas or less, preferably 750 mPas or less, further more preferably 500 mPas or less, measured with a Brookfield RV DVIII viscometer and spindle #3 at 5 rpm and 25° C. under atmospheric pressure.

Compound(s) According to Group a)

Composition A comprises one or more hair dye(s) as compound(s) according to group a).

It is preferred from the viewpoint from commercial availability and dyeing intensity that one or more compound(s) according to group a) is/are oxidative hair dye(s) and/or direct hair dye(s), and/or their salt(s), and/or their mixtures, preferably one or more compound(s) according to group a) is/are oxidative hair dye(s) and/or their salt(s), and/or their mixtures.

Suitable oxidative dye(s) is/are p-phenylenediamine, p-aminophenol, 2,5-diamino-toluene, 2-n-propyl or 2-ethyl-p-phenylenediamine, 2,6-di-methyl-p-phenylene-diamine, 2-(2,5-diaminophenyl) ethanol, 1-amino-4-bis-(2'-hydroxyethyl)amino-benzene, 2-(2-hydroxyethyl amino)-5-aminotoluene, 4,4'-diaminodiphenylamine, 4-aminodiphenylamine, 2-amino-5-N,N-diethyl aminotoluene, 4-amino-N-ethyl-N-isopropyl aniline, 2-chloro-p-phenylenediamine, 1-p-hydroxyethyl-2,5-diamino-4-chlorobenzene, 1-p-hydroxyethyl-2,5-diamino-4-methyl benzene, 2-methoxy-p-phenylenediamine, N,N-diethyl-p-phenylenediamine, 1-amino-4-p-methoxyethyl aminobenzene, 1-dimethyl-amino-4-aminobenzene, 1-hydroxy-2,5-diamino-4-methyl benzene, 1-hydroxymethyl-2,5-diaminobenzene, 1,3-dimethyl-2,5-diaminobenzene, 1,4-diamino isopropyl benzene and/or 1-amino-4-p-hydroxypropyl aminobenzene, 1-hydroxyethyl-4,5-diaminopyrazole, 3,4-diamino-5-hydroxypyrazole, 3,5-diaminopyrazole, 3,5-diamino pyrazol-1-carboxamide, 3-amino-5-hydroxypyrazole, 1-phenyl-2-methylpyrazole, 1-phenyl-3-methylpyrazole-5-one, 3,5-dimethylpyrazole, 3,5-dimethylpyrazole-1-methanol, 3,5-diamino-1,2,4-triazole, 4-aminophenol and the derivatives thereof such as 4-amino-3-methylphenol, 2-chloro-4-aminophenol, 2,6-dichloro-4-aminophenol, 2,4-diamino-phenol, 2,6-dibromo-4-aminophenol, tetraamino pyrimidines, triaminohydroxy pyrimidines, diaminomono- and -dihydroxy pyrimidines, aminotriazines, 5-amino salicylic acid and/or 1,2,4-triamino benzene, 2,5-diaminopyridine, 2,3-diaminopyridine, 2,6-diaminopyridine, 3-amino-2-methyl amino-6-methoxypyridine, 2-dimethyl-5-aminopyridine, 2-dimethyl aminoethyl-3-hydroxypyridine, 2-amino-4,6-dimethyl pyridine, 2-amino-3-hydroxypyridine, 3-amino-2(β-hydroxyethyl amino)-6-methoxy pyridine, 2,6-dimethyl amino-5-aminopyridine, 2-di(hydroxyethyl) amino-5-aminopyridine, 2-hydroxyethyl amino-5-aminopyridine, 4-hydroxy-2,5,6-triaminopyrimidine, 5-amino-2-methylphenol, 2-methyl-5-hydroxyethylaminophenol, 2,4,-diaminophenoxyethanol, 2-amino-4-hydroxyethylaminoanisol, 2-methyl-5-amino-6-chlorphenol, 1,3-bis(2,4-diaminophenoxy)propane, 2-bis(2-hydroxyethyl)aminotoluene, 2-amino-5-methylphenol, resorcinol, 2-methyl-resorcinol, 4-chlororesorcinol, 2-amino-4-chlorophenol, 5-amino-4-methoxy-2-methylphenol, 2-aminophenol, 3-amino-phenol, 1-methyl-2-hydroxy-4-aminobenzene, 3-N,N-dimethyl aminophenol, 2,6-dihydroxy-3,5-dimethoxypyridine, 5-amino-3-methylphenol, 6-amino-3-methylphenol, 1,3-diamino-benzene, 1-amino-3-(2'-hy-droxyethylamino)benzene, 1-amino-3-[bis(2'-hy-droxy-ethyl) amino]benzene, α-naphthol, 4,6-dichlororesorcinol, 1,3-diamino-toluene, 4-hydroxy-1,2-methylenedioxy benzene, 1,5-dihydroxy naphthalene, 1,6-dihydroxy naphthalene, 1,7-dihydroxy naphthalene, 2,7-dihydroxy naphthalene, 1-hydroxy-2-methyl naphthalene, 4-hydroxy-1,2-methyldioxy benzene, 2,4-diamino-3-chlorophenol, 5-amino-2-methoxyphenol and/or 1-methoxy-2-amino-4-(2'-hydroxyethyl amino)-benzene or the water-soluble salts thereof, and mixtures thereof.

Suitable direct hair dye(s) as compound(s) according to group a) is/are Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9, Disperse Violet 1, Acid Red 52, DC Violet 2, DC Red 33, DC Orange 4, DC Red 27, DC Yellow 10, HC Blue 18, HC Red 18, HC Yellow 16, Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green 1, Basic Red 2, Basic Red 12 Basic Red 22, Basic Red 76, Basic Violet 1, Basic Violet 2, Basic Violet 3, Basic Violet 10, Basic Violet 14, Basic Yellow 57, Basic Red 51, Basic Yellow 87, HC Blue 17 and Basic Orange 31. The most preferred ones are Basic Red 51, Basic Yellow 87, Basic Orange 31, HC Blue 17 and Basic Blue 124, HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-amino-6-chloro-4-nitrophenol, and/or their mixtures, and/or their salt(s).

It is preferred from the viewpoint of dyeing intensity that the total concentration of compound(s) according to group a) in composition A is 0.001% by weight or more, more preferably 0.01% by weight or more, still more preferably 0.05% by weight or more, further more preferably 0.1% by weight or more, calculated to the total weight of composition A.

It is preferred from the viewpoint of economic value that the total concentration of compound(s) according to group a) in composition A is 5% by weight or less, more preferably 4% by weight or less, still more preferably 3% by weight or less, further more preferably 2% by weight or less, calculated to the total weight of composition A.

For attaining the above-mentioned effects, it is preferred that the total concentration of compound(s) according to group a) is in the range of 0.001% to 5% by weight, preferably 0.01% to 4% by weight, more preferably 0.05% to 3% by weight, still more preferably 0.1% to 2% by weight, calculated to the total weight of composition A.

Compound(s) According to Group b)

Composition A comprises one or more $C_2$-$C_4$ monohydric, dihydric, or trihydric alcohol(s), and/or their mixtures as compound(s) according to group b), wherein the total concentration of compound(s) according to group b) is 5% by weight or more.

Suitable $C_2$-$C_4$ monohydric, dihydric, or trihydric alcohol(s) are ethanol, isopropanol, n-propanol, n-butanol, tert-butanol, 1,2-propylene glycol, 1,3-propylene glycol, 1,3-butylene glycol, glycerol, and/or their mixtures.

The preferred $C_2$-$C_4$ monohydric, dihydric, or trihydric alcohol(s) from the viewpoint of cosmetic compatibility is/are ethanol, isopropanol, 1,2-propylene glycol, and glycerol.

It is preferred from the viewpoint of composition stability that the total concentration of compound(s) according to group b), preferably the total concentration of ethanol, isopropanol, 1,2-propylene glycol, and glycerol, and/or their mixtures, is 10% by weight or more, more preferably 15% by weight or more, still more preferably 20% by weight or more, calculated to the total weight of composition A.

It is preferred from the viewpoint of composition stability that the total concentration of compound(s) according to group b), preferably the total concentration of ethanol, isopropanol, 1,2-propylene glycol, and glycerol, and/or their mixtures, is 60% by weight or less, more preferably 50% by weight or less, still more preferably 45% by weight or less, calculated to the total weight of composition A.

For attaining the above-mentioned effects, it is preferred that the total concentration of compound(s) according to group b) is in the range of in the range of 10% to 60% by weight, preferably in the range of 15% to 50% by weight, still more preferably in the range of 20% to 45% by weight, calculated to the total weight of composition A.

Compound(s) According to Group c)

Composition A comprises one or more non-ionic surfactant(s) having an HLB value of 11 or less as compound(s) according to group c).

For the purpose of the present invention, the HLB value is calculated by Griffin's well-established method.

It is preferred from the viewpoint of composition stability that one or more compound(s) according to group c) have an HLB of 8 or less, more preferably of 7 or less, still more preferably of 6 or less.

Suitable compound(s) according to group c) is/are ethoxylated saturated or unsaturated fatty alcohol(s), and/or their mixtures, preferably it is an ethoxylated saturated or unsaturated fatty alcohol(s) having a carbon chain length in the range of $C_8$ to $C_{18}$, preferably in the range of $C_{10}$ to $C_{14}$, more preferably in the range of $C_{12}$ to $C_{14}$.

Suitable compound(s) according to group c) are Laureth-2, Laureth-3, Laureth-4, Deceth-2, Deceth-3, Deceth-4, and/or their mixtures.

The most preferred compound(s) according to group c) is Laureth-2.

It is preferred from the viewpoint of composition stability that composition A comprises one or more compound(s) according to group c) at a total concentration of 1% by weight or more, more preferably 5% by weight or more, still more preferably 10% by weight or more, further more preferably 15% by weight or more, calculated to the total weight of composition A.

It is preferred from the viewpoint of composition stability that composition A comprises one or more compound(s) according to group c) at a total concentration of 40% by weight or less, more preferably 35% by weight or less, still more preferably 30% by weight or less, further more preferably 25% by weight or less, calculated to the total weight of composition A.

For attaining the above-mentioned effects, it is preferred that composition A comprises one or more compound(s) according to group c) at a total concentration in the range of 1% to 40% by weight, preferably in the range of 5% to 35% by weight, further more preferably 10% to 30% by weight, still more preferably 15% to 25% by weight, calculated to the total weight of composition A.

Compound(s) According to Group d)

Composition A comprises one or more quaternary ammonium surfactant(s) according to the following structure:

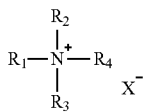

wherein $R_1$ and $R_2$ are independently selected from $C_1$ to $C_{22}$ alkyl or alkylene with the provision that at least $R_1$ is selected from $C_{17}$ to $C_{22}$ alkyl or alkylene, $R_3$ and $R_4$ are independently selected from $C_1$ to $C_4$ alkyl or alkylene, and $X^-$ is a halogen, sulfate or methosulfate anion, as compound (s) according to group d).

Suitable compound(s) according to group d) is/are steartrimonium chloride, steartrimonium bromide, steartrimonium methosulfate, behentrimonium chloride, behentrimonium bromide, behentrimonium methosulfate, distearoyl dimonium chloride, distearoyl dimonium bromide, and/or their mixtures, more preferably they are steartrimonium chloride and behentrimonium chloride, and/or their salt(s), more preferably it is steartrimonium chloride.

It is preferred from the viewpoint of viscosity upon mixing with composition B that composition A comprises one or more compound(s) according to group d) at a total concentration of 0.5% by weight or more, preferably 1% by weight or more, more preferably 1.5% by weight or more, calculated to the total weight of composition A.

It is preferred from the viewpoint of viscosity upon mixing with composition B that composition A comprises one or more compound(s) according to group d) at a total concentration of 10% by weight or less, preferably 8% by weight or less, more preferably 6% by weight or less, calculated to the total weight of composition A.

For attaining the above-mentioned effects, it is preferred that the total concentration of one or more compound(s) according to group d) is in the range of 0.5% to 10% by weight, preferably 1% to 8% by weight, more preferably in the range of 1.5% to 6% by weight, calculated to the total weight of composition A.

Compound(s) According to Group e)

Composition A comprises one or more quaternary ammonium surfactant(s) according to the following structure as compound(s) according to group e):

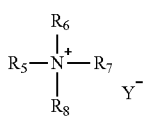

Wherein $R_5$ and $R_6$ are independently selected from $C_1$ to $C_{16}$ alkyl or alkylene with the provision that at least $R_5$ is selected from $C_8$ to $C_{16}$ alkyl or alkylene, $R_7$ and $R_8$ are independently selected from $C_1$ to $C_4$ alkyl or alkylene, and $Y^-$ is a halogen, sulfate or methosulfate anion.

Suitable compound(s) according to group e) is/are cetrimonium chloride, cetrimonium bromide, dodecyltrimonium chloride, and/or their mixtures, preferably they is/are cetrimonium chloride and/or cetrimonium bromide, and/or their mixtures.

The total concentration of one or more compound(s) according to group e) is in the range of 0.5% to 10% by weight, calculated to the total weight of composition A.

It is preferred from the viewpoint of viscosity upon mixing with composition B that composition A comprises one or more compound(s) according to group e) at a total concentration of 1% by weight or more, further more preferably 1.5% by weight or more, calculated to the total weight of composition A.

It is preferred from the viewpoint of viscosity upon mixing with composition B that composition A comprises one or more compound(s) according to group e) at a total concentration of 8% by weight or less, more preferably of 6% by weight or less, calculated to the total weight of composition A.

For attaining the above-mentioned effects, it is preferred that composition A comprises one or more compound(s) according to group e) at a total concentration in the range of 1% to 8% by weight, preferably in the range of 1.5% to 6% by weight, calculated to the total weight of composition A.

Preferably, from the viewpoint of preventing dripping upon mixture with composition B, the weight ratio of compound(s) according to group d) to compound(s) according to group e) is in the range of 10:1 to 1:10, more preferably in the range of 7:1 to 1:7, still more preferably in the range of 5:1 to 1:5, further still more preferably in the range of 3:1 to 1:3.

Kit-of-Parts

The present invention is also directed to a kit-of-parts for dyeing keratin fibers, preferably for dyeing human keratin fibers, more preferably for dyeing human hair, comprising:
 composition A as defined above,
 an aqueous acidic composition B having a pH in the range of 1 to 6 and optionally comprising one or more oxidizing agent(s), preferably hydrogen peroxide,
 an optional bleaching composition C.

It is preferred from the viewpoint of stability that compositions A and B are mixed directly prior to application onto keratin fibers.

It is preferred from the viewpoint of storage stability and safety of composition B that the pH is 1.25 or more, more preferably 1.5 or more, further more preferably 2 or more.

It is preferred from the viewpoint of storage stability of the composition that the pH of composition B is 5 or less, more preferably 4 or less, further more preferably 3 or less.

For attaining the above-mentioned effects, it is preferred that the pH of composition B is in the range of 1.25 to 5, more preferably in the range of 1.5 to 4, further more preferably in the range of 2 to 3.

It is further preferred from the viewpoint of product performance that the concentration of hydrogen peroxide in composition B, if present, is 1% by weight or more, more preferably 3% by weight or more, further more preferably 6% by weight or more, still more preferably 9% by weight or more, calculated to the total weight of composition B.

It is further preferred from the viewpoint of product performance and user safety that the concentration of hydrogen peroxide in composition B, if present is 20% by weight or less, more preferably 15% by weight or less, further more preferably 12% by weight or less, calculated to the total weight of composition B.

For attaining the above-mentioned effects, it is preferred that the concentration of hydrogen peroxide in composition B, if present, is in the range of 1% to 20% by weight, more preferably 3% to 15% by weight, further more preferably 6% to 12% by weight, still more preferably in the range of 9% to 12% by weight, calculated to the total weight of composition B.

Suitable mixing rations by weight of compositions A and B are in the range of 5:1 to 1:5, preferably in the range of 3:1 to 1:3, more preferably in the range of 2:1 to 1:2.

The optional bleaching composition C may be a bleaching powder composition or an aqueous lightening composition.

The bleaching powder composition may comprise one or more persalt(s) and/or peroxy salt(s). Suitable persalts and/or peroxy salts are sodium persulfate, potassium persulfate, ammonium persulfate, earth alkali peroxides such as magnesium peroxide, melamine peroxide or urea peroxide or phthalimidoperoxy hexanoic acid. The preferred persalts from the viewpoint of bleaching power are sodium, potassium, and ammonium persulfate.

It is preferred from the viewpoint of bleaching power and cosmetic safety that the total concentration of persalts and/or peroxy salts in the bleaching powder composition is in the range of 10% to 80% by weight, preferably 15% to 70% by weight, more preferably 20% to 60% by weight, and still more preferably 25% to 60% by weight, calculated to the total weight of the bleaching composition C.

Independent of the product form of the bleaching composition C, it is preferred that is comprises one or more alkalizing agent(s), suitably inorganic and/or organic alkalizing agent(s), and/or their mixtures.

Suitably, inorganic alkalizing agent(s) are metasilicates, carbonates, and/or bicarbonates, and/or their alkali or earth alkali salts, and/or their mixtures.

Suitably, organic alkalizing agent(s) are alkyl- or alkanolamines according to the general structure

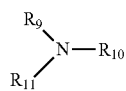

wherein $R_9$, $R_{10}$, and $R_{11}$ are same or different H, from $C_1$ to $C_4$, $C_3$ to $C_4$ unsaturated alkyl, $C_3$ to $C_4$ branched alkyl, $C_1$ to $C_4$ hydroxyl alkyl, $C_3$ to $C_4$ unsaturated hydroxyl alkyl, $C_3$ to $C_4$ branched hydroxyl alkyl, with the condition that at least one of $R_9$, $R_{10}$, or $R_{11}$ is different from H, and/or their mixtures.

Suitable organic alkalizing agents are monoethanolamine, diethanolamine, triethanolamine, monomethylamine, dimethylamine, trimethylamine, monoethylamine, diethylamine, and 2-aminomethyl propanol.

The most preferred organic alkalizing agent(s) for bleaching composition C are selected from monoethanolamine, 2-aminomethyl propanol, and sodium metasilicate, and/or their mixtures.

It is preferred from the viewpoint of alkalinity and stability that composition C may comprise one or more alkalizing agent(s) at a total concentration in the range of 0.25% to 30% by weight, preferably 0.5% to 25% by weight, more preferably 1% to 20% by weight, calculated to the total weight of the bleaching composition C.

Ready-to-Use Composition

The present invention is also directed to a ready-to-use composition having a pH in the range of 6 to 12 comprising composition A as defined above and composition B as defined above.

It is preferred from the viewpoint of dyeing intensity that the pH of the ready-to-use composition is in the range of 6.5 to 11.5, more preferably in the range of 7 to 11.

The ready-to-use composition is prepared directly prior to application onto keratin fibers. By mixing compositions A and B, the viscosity of the ready-to-use composition increases with respect to the viscosity of composition A to a range of 1,000 to 30,000 mPas, preferably in the range of 1,500 to 20,000 mPas, more preferably in the range of 2,000 to 10,000 mPas, measured with a Brookfield RV DVIII viscometer and spindle #3 at 5 rpm and 25° C. under atmospheric pressure.

Dyeing Method

The present invention is also directed to a method for dyeing keratin fibers, preferably human keratin fibers, more preferably human hair, comprising the steps of:
 i) mixing composition A as defined above with an acidic aqueous composition B as defined above to yield a ready-to-use composition having a pH in the range of 6 to 12,
 ii) applying the ready-to-use composition onto keratin fibers and leaving it for a time period in the range of 1 to 60 min,
 iii) rinsing off the ready-to-use composition,
 iv) optionally shampooing and drying the keratin fibers.

Preferably, the pH of the ready-to-use composition in step i) is in the range of 6.5 to 11.5, more preferably in the range of 7 to 11.

Preferably, the ready-to-use composition is left on keratin fibers in step ii) for a time period in the range of 2 min to 45 min, more preferably for a time period in the range of 5 min to 35 min.

The following examples are to illustrate the present invention and not to limit it.

EXAMPLES

TABLE 1

The following compositions A were prepared:

| | Ingredients | Inv. ex. 1 | Inv. ex. 2 | Inv. ex. 3 | Inv. ex. 4 | Inv. ex. 5 | Inv. ex. 6 | Comp. ex. 1 | Comp. ex. 2 |
|---|---|---|---|---|---|---|---|---|---|
| | | [% by weight AM] | | | | | | | |
| a) | 4-Amino-2-Hydroxytoluene | 0.045 | 0.045 | 0.045 | 0.045 | 0.045 | 0.045 | 0.045 | 0.045 |
| a) | Toluene-2,5-diamine sulfate | 0.052 | 0.052 | 0.052 | 0.052 | 0.052 | 0.052 | 0.052 | 0.052 |
| b) | Ethanol | 1.0 | 1.0 | 5.0 | 1.0 | 1.0 | 1.0 | 1.0 | 1.0 |
| b) | Isopropanol | 15.0 | 15.0 | 25.0 | 15.0 | 15.0 | 15.0 | 15.0 | 15.0 |
| b) | 1,2-Propylene glycol | 8.0 | 8.0 | 1.0 | 8.0 | 8.0 | 8.0 | 8.0 | 8.0 |
| c) | Laureth-2 | 15.0 | 15.0 | 25.0 | 15.0 | 15.0 | 15.0 | 15.0 | 15.0 |
| d) | Steartrimonium chloride | 1.25 | — | 1.25 | 1.5 | 0.5 | 5.0 | — | 2.5 |
| d) | Behentrimonium chloride | — | 1.25 | — | — | — | — | — | — |
| e) | Dodecyltrimonium chloride | — | 1.25 | — | — | — | — | — | — |

TABLE 1-continued

| | The following compositions A were prepared: | | | | | | | | |
|---|---|---|---|---|---|---|---|---|---|
| e) | Cetrimonium chloride | 1.25 | — | 1.25 | 0.5 | 1.5 | 5.0 | 2.5 | — |
| — | NaOH/HCl | | | | Ad pH 8.0 | | | | |
| — | Water | | | | Ad 100.0 | | | | |
| Evaluation | Transparency | 5 | 5 | 5 | 5 | 5 | 5 | 5 | 5 |
| | Wet hair feel | 5 | 6 | 5 | 4 | 5 | 6 | 5 | 3 |
| | Dry hair feel | 5 | 5 | 5 | 5 | 4 | 6 | 3 | 5 |
| | Stability at 25° C. | 5 | 5 | 5 | 5 | 5 | 5 | 4 | 5 |
| | Dripping of ready-to-use mixture after application | 3 | 3 | 3 | 3 | 3 | 4 | 1 | 2 |
| | Total scores | 23 | 24 | 23 | 22 | 22 | 26 | 17 | 20 |

| Composition B | % by weight |
|---|---|
| Hydrogen peroxide | 6.0 |
| EDTA | 0.5 |
| Phosphoric acid | ad pH 2.5 |
| Water | ad 100.0 |

Compositions A of table 1 and composition B as above were mixed in a weight ratio of 1:1 to yield a ready-to-use composition having a pH of 7.0. The ready-to-use compositions had a viscosity in the range of 1,500 mPas to 4,000 mPas measured with a Brookfield RV DVIII viscometer and spindle #3 at 5 rpm and 25° C. under atmospheric pressure.

Discussion of Results

The examples of table 1 illustrated, that the inventive compositions had higher total scores. In particular, scores in dry hair feel as well as dripping of the ready-to-use mixture were much higher than the scores of the comparative compositions.

Methods

Preparation of Compositions

Compound(s) according to group c) were dissolved in compound(s) according to group b), then the other ingredients were added. Finally, the alcoholic composition was diluted with water.

Hair Dyeing

To prepare a ready-to-use composition, each of the compositions from table 1 were mixed with composition B displayed above having a pH of 2.5 in a weight ratio of 1:1. 2 g of the resulting ready-to-use compositions were applied to goat hair (2.5 g per bundle, 21 cm long) and left for 20 min at ambient temperature. The hair was then rinsed-off with water and blow-dried.

Dripping

To prepare a ready-to-use composition, each of the compositions from table 1 were mixed with composition B displayed above having a pH of 2.5 in a weight ratio of 1:1. 2 g of the resulting ready-to-use compositions were applied to forearm, and dripping was monitored over 5 minutes.

Evaluations 5 experts were independently of each other asked to rate the colored hair streaks and the results on the forearms. Experts were not informed on the treatment groups prior to their judgement. They were asked to assign an integer value to each property as listed in table 1. For wet and dry hair feel, a scale in the range of 1 to 10 was given. For transparency, stability, and dripping, a scale of 1 to 5 was given. Higher numbers represented the best performance. The reported values for each group are modal values.

The invention claimed is:

1. An aqueous-alcoholic dyeing composition A for keratin fibers having a pH in the range of 6 to 12 comprising:
at least one hair dye,
at least one alcohol (b) selected from the group consisting of a C2-C4 monohydric alcohol, a C2-C4 dihydric alcohol, and a C2-C4 trihydric alcohol, and/or their mixtures,
at least one non-ionic surfactant having an HLB value of 11 or less, and
at least one quaternary ammonium surfactant according to the following Formula (I):

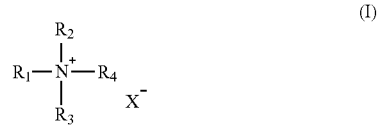

(I)

wherein $R_1$ is selected from the group consisting of a C17 to C22 alkyl group and a C17 to C22 alkylene group, $R_2$ is selected from the group consisting of a C1 to C22 alkyl group and a C1 to C22 alkylene group, $R_3$ and $R_4$ are each independently selected from the group consisting of a C1 to C4 alkyl group and a C1 to C4 alkylene group, and X- is selected from the group consisting of a halide anion, a sulfate anion, and a methosulfate anion, wherein a total concentration of alcohol (b) is 5% by weight or more, based on a total weight of aqueous-alcoholic dyeing composition A, wherein aqueous-alcoholic dyeing composition A comprises at least one quaternary ammonium surfactant according to the following Formula (II):

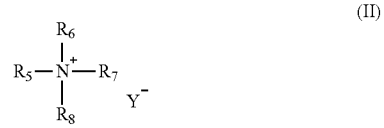

(II)

wherein $R_5$ is selected from the group consisting of a C8 to C16 alkyl group and a C8 to C16 alkylene group, $R_6$ is selected from the group consisting of a C1 to C16 alkyl group and a C1 to C16 alkylene group, $R_7$ and $R_8$ are each independently selected from the group consisting of a C1 to C4 alkyl group and a C1 to C4 alkylene group, and Y- is selected from the group consisting of a halogen halide anion, a sulfate anion, and a methosulfate anion, and wherein a total concentration of the at least one quaternary ammonium surfactant according to Formula (II) is in a range of 0.5% to 10% by weight, based on a total weight of aqueous-alcoholic dyeing composition A.

2. The aqueous-alcoholic dyeing composition A according to claim 1, wherein the pH of aqueous-alcoholic dyeing composition A is in the range of 7 to 11.

3. The aqueous-alcoholic dyeing composition A for according to claim 1, wherein the at least one hair dye is selected from the group consisting of an oxidative hair dye, a direct hair dye, and a salt thereof.

4. The aqueous-alcoholic dyeing composition A according to claim 1, wherein the at least one alcohol (b) is selected from the group consisting of ethanol, isopropanol, n-propanol, n-butanol, tert-butanol, 1,2-propylene glycol, 1,3-propylene glycol, 1,3-butylene glycol, and glycerol.

5. The aqueous-alcoholic dyeing composition A according to claim 1, wherein the aqueous-alcoholic dyeing composition A is transparent judged by the naked human eye at an optical path length of 1 cm.

6. The composition according to claim 1, wherein the at least one have non-ionic surfactant has an HLB of 8 or less.

7. The aqueous-alcoholic dyeing composition A according to claim 1, wherein the at least one non-ionic surfactant is an ethoxylated saturated or unsaturated fatty alcohol.

8. The aqueous-alcoholic dyeing composition A according to claim 1, wherein the quaternary ammonium surfactant according to Formula (I) is at least one selected from the group consisting of steartrimonium chloride, steartrimonium bromide, steartrimonium methosulfate, behentrimonium chloride, behentrimonium bromide, behentrimonium methosulfate, distearoyl dimonium chloride, and distearoyl dimonium bromide.

9. The aqueous-alcoholic dyeing composition A according to claim 1, wherein a total concentration of the quaternary ammonium surfactant according to Formula (I) is in a range of 0.5% to 10% by weight, based on a total weight of aqueous-alcoholic dyeing composition A.

10. The aqueous-alcoholic dyeing composition A according to claim 1, wherein the quaternary ammonium surfactant according to the Formula (II) is at least one selected from the group consisting of cetrimonium chloride, cetrimonium bromide, and dodecyltrimonium chloride.

11. The aqueous-alcoholic dyeing composition A according to claim 1, wherein a total concentration of the quaternary ammonium surfactant according to the Formula (II) is in a range of 1% to 8% by weight, based on a total weight of aqueous-alcoholic dyeing composition A.

12. The aqueous-alcoholic dyeing composition A according to claim 1, wherein a weight ratio of the quaternary ammonium surfactant according to the Formula (I) to the quaternary ammonium surfactant according to the Formula (II) is in a range of 10:1 to 1:10.

13. A kit-of-parts for dyeing keratin fibers, comprising:
the aqueous-alcoholic dyeing composition A of claim 1,
an aqueous acidic composition B having a pH in a range of 1 to 6 and optionally comprising an oxidizing agent, and
an optional bleaching composition C.

14. A ready-to-use composition having a pH in a range of 6 to 12 comprising the aqueous-alcoholic dyeing composition A of claim 1 and an aqueous acidic composition B having a pH in a range of 1 to 6 and optionally comprising an oxidizing agent.

15. The ready-to-use composition according to claim 14, wherein a viscosity of the ready-to-use composition is in a range of 1,000 to 30,000 mPas, measured with a Brookfield RV DVIII viscometer and spindle #3 at 5 rpm and 25° C. under atmospheric pressure.

16. A method for dyeing keratin fibers comprising the steps of:
mixing the aqueous-alcoholic dyeing composition A of claim 1 with an acidic aqueous composition B having a pH in a range of 1 to 6 and optionally comprising an oxidizing agent to yield a ready-to-use composition having a pH in a range of 6 to 12,
applying the ready-to-use composition onto keratin fibers and leaving it for a time period in the range of 1 to 60 min,
rinsing off the ready-to-use composition, and
optionally shampooing and drying the keratin fibers.

17. The aqueous-alcoholic dyeing composition A according to claim 1, wherein a total concentration of alcohol (b) is in a range of 15% to 60% by weight, based on a total weight of aqueous-alcoholic dyeing composition A.

18. The aqueous-alcoholic dyeing composition A according to claim 1, wherein the non-ionic surfactant is an ethoxylated saturated or unsaturated fatty alcohol having a carbon chain length in the range of C8 to C18.

19. The aqueous-alcoholic dyeing composition A according to claim 1, wherein a weight ratio of the quaternary ammonium surfactant according to the Formula (I) to the quaternary ammonium surfactant according to the Formula (II) is in a range of 3:1 to 1:3.

20. An aqueous-alcoholic dyeing composition A for keratin fibers having a pH in the range of 6 to 12 comprising:
an oxidative hair dye,
an alcohol (b) selected from the group consisting of ethanol, isopropanol, 1,2-propylene glycol, present in a total concentration in a range of 15% to 60% by weight, based on a total weight of aqueous-alcoholic dyeing composition A,
a non-ionic surfactant having an HLB value of 11 which is a C12 to C14 ethoxylated saturated fatty alcohols,
a quaternary ammonium surfactant selected from a steartrimonium halide salt, a steartrimonium sulfate salt, a steartrimonium methosulfate salt, a behentrimonium halide salt, a behentrimonium sulfate salt, and a behentrimonium methosulfate salt, and
a quaternary ammonium surfactant selected from a dodecyltrimonium halide salt, a dodecyltrimonium sulfate salt, a dodecyltrimonium methosulfate salt, a cetrimonium halide salt, a cetrimonium sulfate salt, and a cetrimonium methosulfate salt, at a total concentration in a range of 0.5% to 10% by weight, based on a total weight of aqueous-alcoholic dyeing composition A.

* * * * *